United States Patent
Grünig et al.

[11] Patent Number: 6,120,508
[45] Date of Patent: Sep. 19, 2000

[54] RASP DETERMINED FOR ONE-TIME USE, PARTICULARLY BONE RASP AS WELL AS PROCESS FOR ITS PRODUCTION

[75] Inventors: Daniel Grünig, Malters; Albert Geisser, Ennetbürgen, both of Switzerland

[73] Assignee: IMT Integral Medizintechnik AG, Ennetburgen, Switzerland

[21] Appl. No.: 09/335,576

[22] Filed: Jun. 18, 1999

[30] Foreign Application Priority Data

Jun. 19, 1998 [EP] European Pat. Off. .............. 98111300

[51] Int. Cl.⁷ ............................................. A61F 5/04
[52] U.S. Cl. ................................... 606/85; 606/79
[58] Field of Search ................. 606/80, 84, 85, 606/79, 96, 89, 87, 86, 99, 100; 132/76.4, 76.5; 408/227, 228, 229, 230, 231

[56] References Cited

U.S. PATENT DOCUMENTS

| | | | |
|---|---|---|---|
| D. 273,806 | 5/1984 | Bolesky et al. | D24/28 |
| 959,213 | 5/1910 | Ganz | 132/76.4 |
| 4,466,429 | 8/1984 | Loscher et al. | 128/92 E |
| 4,811,632 | 3/1989 | Sayler | 606/85 |
| 5,006,121 | 4/1991 | Hafeli | 606/85 |
| 5,100,267 | 3/1992 | Salyer | 407/54 |
| 5,124,106 | 6/1992 | Morr et al. | 264/221 |
| 5,441,501 | 8/1995 | Keynon | 606/85 |
| 5,454,815 | 10/1995 | Geisser et al. | 606/85 |
| 5,814,049 | 9/1998 | Pratt et al. | 606/80 |

FOREIGN PATENT DOCUMENTS

| | | | |
|---|---|---|---|
| 0 136 079 A3 | 4/1985 | European Pat. Off. | A61B 17/16 |
| 0 296 986 A1 | 12/1988 | European Pat. Off. | A61B 17/16 |
| 0 331 626 A2 | 9/1989 | European Pat. Off. | A61B 17/16 |
| 0 472 132 A1 | 2/1992 | European Pat. Off. | A61B 17/54 |
| 0 574 701 A1 | 12/1993 | European Pat. Off. | A61B 17/16 |
| 2 274 267 | 2/1976 | France | A61C 5/04 |
| 2 547 192 | 12/1984 | France | A61B 17/16 |
| 3801678 | 8/1989 | Germany | 606/85 |
| 3801678 C1 | 8/1989 | Germany | A61B 17/16 |
| 3907256 A1 | 9/1990 | Germany | A61F 2/46 |

Primary Examiner—Pedro Philogene
Attorney, Agent, or Firm—Ohlandt, Greeley, Ruggiero & Perle; George W. Rauchfuss, Jr.

[57] ABSTRACT

The rasp (1) has a support unit (3), which is surrounded by an envelope (4) of metal, which forms rasp teeth (5). This mode of construction permits the use of very thin sheet for envelope (4) and cost-favorable plastic for support unit (3), which makes possible the formation of a stable, well-cutting, disposable rasp.

14 Claims, 2 Drawing Sheets

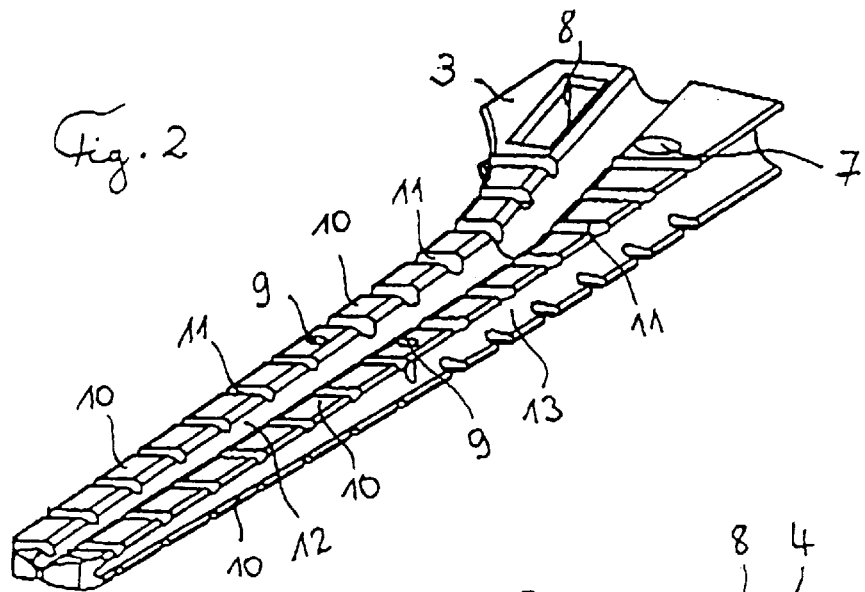
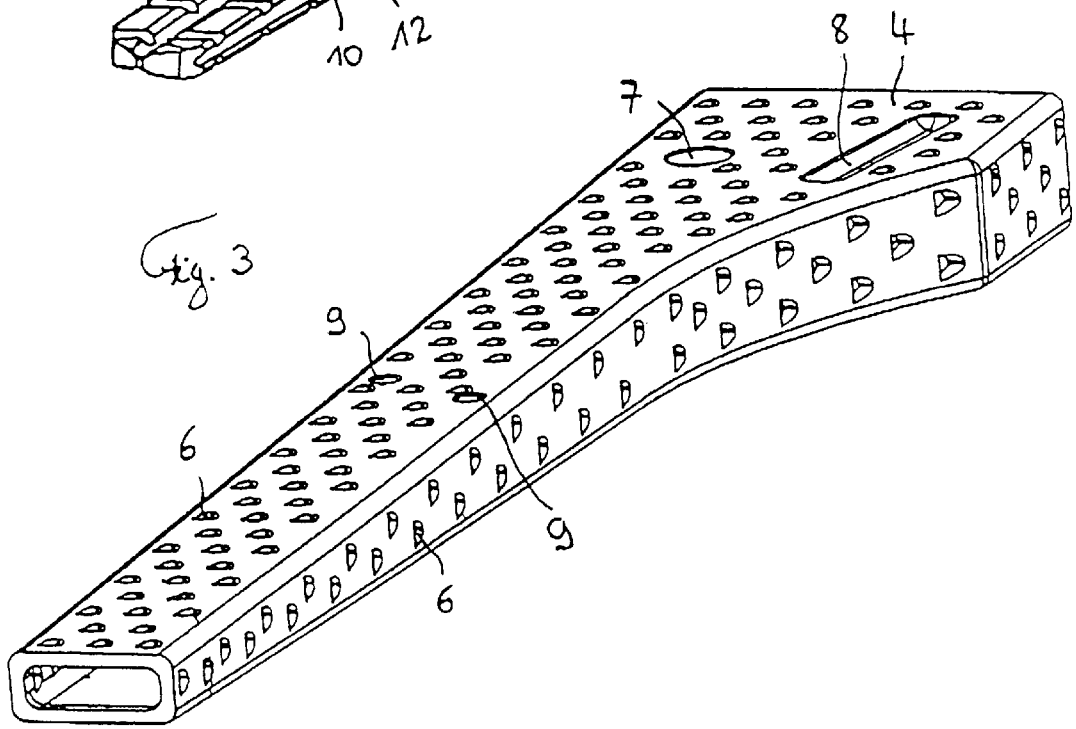
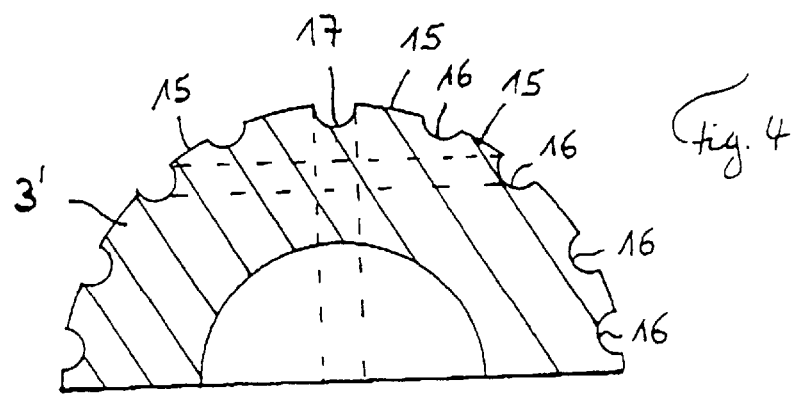

RASP DETERMINED FOR ONE-TIME USE, PARTICULARLY BONE RASP AS WELL AS PROCESS FOR ITS PRODUCTION

CROSS REFERENCE TO RELATED APPLICATIONS

This application claims the priority of the European Patent Application No. 98111300.4 filed Jun. 19, 1998, the disclosure of which is incorporated herein by reference in its entirety.

BACKGROUND OF THE INVENTION

The invention concerns a rasp according to the preamble of claim 1. Further, the invention concerns a process for the production of a rasp according to the preamble of claim 9.

Rasps, which are suitable for processing, i.e., filing and rasping bone material, and are applied, e.g., in the implanting of hip joint prostheses, are known in various designs. A bone rasp of metal is known from DE-A-3,907,256, which has a channel on the inside for receiving the filed-down material. A rasp with hollow space is also known from EP-A-0,331,626. These rasps are conventionally produced from steel and are provided for multiple use, which requires a corresponding cleaning. This is labor-intensive and nevertheless does not lead to the complete removal of depositions. Also, the subsequent sterilization of the rasp does not lead to the removal of such depositions, and it is, in fact possible that infectious material, particularly infectious protein, can maintain an infectious potential even after the sterilization process. Therefore, disposable rasps have already been proposed for only one-time use. EP-A-0 563, 585 and EP-A-0 574,701 show disposable rasps made of plastic. In the production of such rasps from biocompatable plastic material, however, problems may arise with the rasp action, particularly in hard bone material and with longer application times. U.S. Pat. No. 5,100,267 shows a disposable rasp in hemisphere form, in which the hemisphere is designed normally as an intrinsically stable part and a disk-shaped base of plastic is attached to this, on which base the adapter part is arranged for clamping the rasp in a drive tool. The intrinsically stable design of the metal rasp part leads to the use of relatively thick surgical steel of more than 1 mm thickness, which represents a high expenditure for a disposable rasp. Rasps produced according to this principle would be of approximately equal expense as standard rasps for multiple use, but with statically more unfavorable shapes than the hemisphere.

BRIEF SUMMARY OF THE INVENTION

The invention is thus based on the task of creating a rasp, which does not have the named disadvantages. In particular, a disposable rasp for bone material will be created, which does not have the named disadvantages.

This is achieved in the case of a rasp of the type named initially by the characterizing features of claim 1.

Due to the fact that an inner support unit is provided, which essentially corresponds to the shape of the rasp, the outer envelope of metal, which forms the rasp teeth, can be of a very thin wall, when compared with conventional rasps. This decreases the material expenditure and can also reduce the production expenditure. Further, rasps with thin-walled rasp teeth producing a particularly good cutting power, can also be provided in this way.

Most preferably, the support unit is provided with ribs, which form the bearing surfaces for the envelope and form hollow spaces between them, in which bone material removed by the rasp can enter through the openings in the rasp teeth.

The invention is further based on the task of creating a process for the production of a rasp, which permits simple and cost-favorable production.

This is achieved by a process of the type named initially with the characterizing features of claim 9.

BRIEF DESCRIPTION OF THE DRAWINGS

Examples of embodiment of the invention based on the drawings will be explained in more detail below. Here:

FIG. 2 shows a perspective view of the support unit;

FIG. 3 shows a perspective view of the envelope of the rasp; and

FIG. 4 shows a vertical section through another form of embodiment of the rasp.

DETAILED DESCRIPTION OF THE INVENTION

Figure 1:
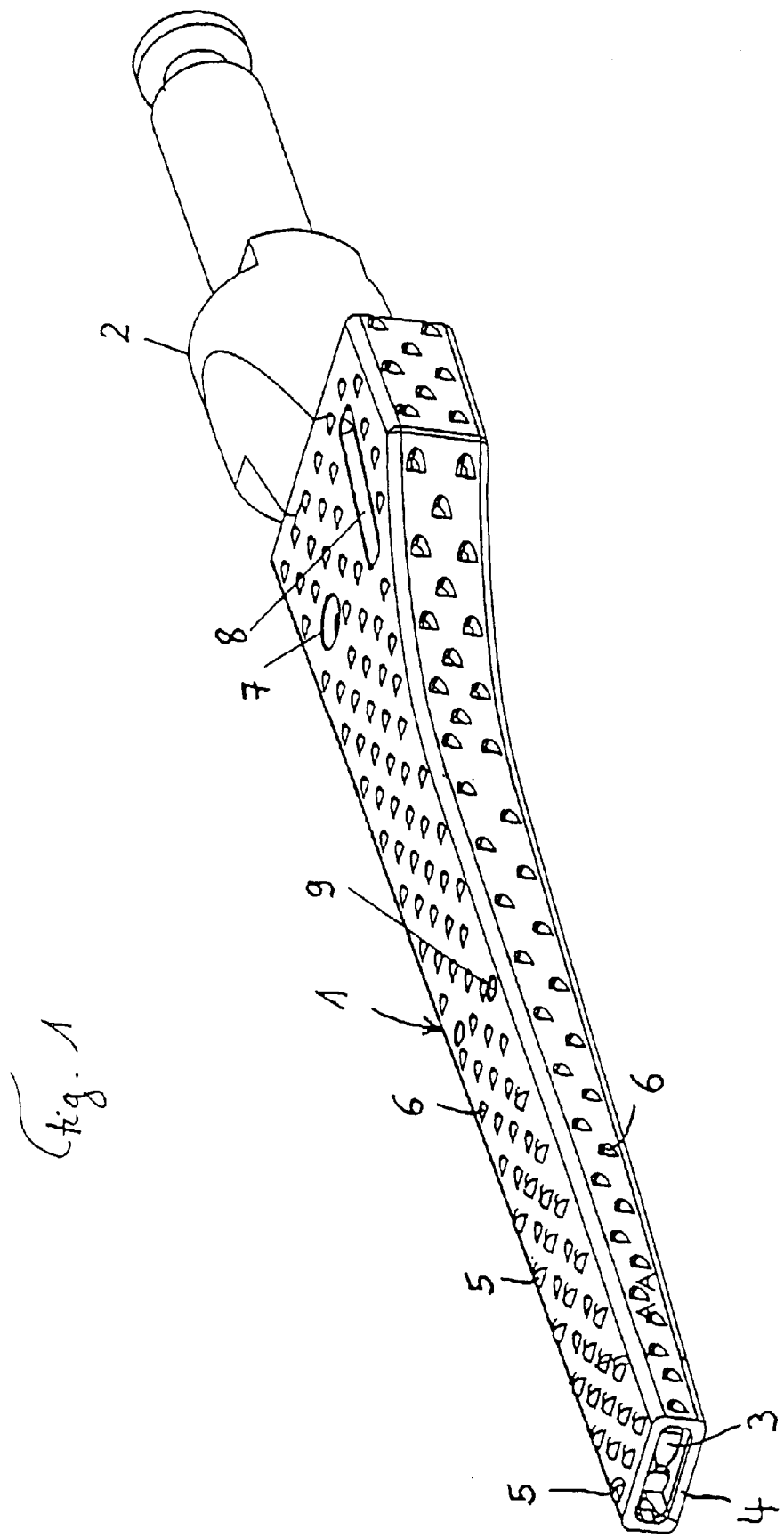
FIG. 1 shows a perspective view of a first form of embodiment of the rasp.

FIG. 1 shows a perspective view of a bone rasp 1 with a cutaway tip; thus a view is given of the inside. An adapter 2 is attached to bone rasp 1, and by means of this adapter, the bone rasp can be coupled to a drive tool, which can move the bone rasp in an oscillating motion in the known way. The bone rasp is formed according to the invention with an inner support unit 3 and an outer envelope 4. The outer envelope is comprised of metal and has rasp teeth 5, of which only a part are shown as raised rasp teeth and the other teeth 6, for purposes of the drawing, are only indicated as depressions. Rasp 1 has a shape known in and of itself with a front end running into a point or blunt tip and a back end expanding toward the back. In the example shown, recesses are provided on the inner unit for attaching to envelope 4, in which recesses the metal material of envelope 4 can be pressed in order to achieve a joining of the two parts. This method of attachment is shown in FIG. 1 by recesses 7, 8 and 9.

FIG. 2 shows the support unit 3 of the rasp, also in perspective presentation, whereby the support unit is rotated around its long axis by 180° relative to the position of FIG. 1. Support unit 3 essentially has the form of rasp 1, whereby the support unit in the present example does not extend up to the tip of rasp 1, but rather ends prior to the tip. Thus in this example the frontmost part of the rasp is formed only by the envelope alone. The support unit forms a support for the envelope and can be adapted fully on its surface to the inside wall of the envelope. It is, of course, preferred that the support unit, as shown in FIG. 2, has a multiple number of support elements 10, which can be denoted, e.g., as ribs, and which are separated from one another by recesses 11, 12, and 13. In the example shown, recesses 12 and 13 form running channels in the longitudinal direction of the rasp, whereas recesses 11 form channels lying crosswise between ribs 10 which channels join the longitudinal channels 12 and 13 with one another. Channels 11–13 permit the material removed by the rasp to pass through the openings of the rasp teeth to the inside of the rasp and collect there in the channels. As a rule, the volume of the channels is sufficient to take up all of the material that enters during the rasping process. However, an aspiration of the material from the channels can also be provided, which is not shown here, however.

FIG. 3 shows the envelope, which is arranged around support unit 3 of FIG. 2 and forms the rasp together with the latter. The envelope is drawn in FIG. 3 also without the tip of the rasp. The shape of the tip, which is not shown, can thus correspond to known rasp tip forms and therefore will not be represented further here.

Plastics or also aluminum are considered for the material of the inner support unit 3. In particular, a series of biocompatable plastics are known, which are utilized for surgical elements, which can also form the inside unit 3 of the rasp. Element 3 is produced as a rule by an injection molding process. Envelope 4 can be formed, e.g., by a deep-drawing of a sheet metal in the longitudinal direction of the rasp. Several deep-drawing steps may be necessary for this. There then results a one-piece envelope, as it is shown in FIG. 3. The rasp teeth are shaped by inserting and withdrawing corresponding material segments in this envelope, as is basically known. After this, envelope 4 and support unit 3 may be joined together by shifting the envelope over the support unit and these two components are joined with each other, e.g., by pressing the metal envelope parts into recesses 7, 8 and 9 of the support unit, as this is shown in FIG. 1. Other fastening possibilities, by gluing or by means of screws or rivets, of course, are also possible. Fastening results in solid unmoveable joining between support unit and envelope.

The envelope can further also be formed of several parts, e.g., by deep drawing of two tub-shaped halves, which are then joined to one another. Rasp teeth can also be formed in such a deep-drawing or punching operation. The joining of the two parts of the envelope can be produced by scarf-joining, welding, screws, or by fastening means to support unit 3, so that support unit 3 attaches both halves of envelope 4, and thus holds the envelope together. Corresponding grooves for the uptake of tabs or tacks of the envelope parts can be provided in support unit 3. A rigid, unmoveable joining between support unit and envelope is also produced in this way.

The material of the envelope is formed of conventional surgical steel or another metal. Since the envelope according to the invention forms the rasp together with support unit 3, the possibility exists of designing the envelope very thin, which is not possible in a conventional rasp without support unit. Thus, e.g., the material of the envelope may be comprised of a sheet of only 0.2 mm to 0.8 mm thickness. The sheet, however, may also have a thickness of up to 1 mm or, if it is desired, a thickness also of e.g., up to 4 mm, as in the conventional manner. It is preferred, however, for a disposable rasp, to keep the material expenditure for the envelope 4 as small as possible, which can be done thanks to the support unit, which can be produced from cost-favorable plastic. Likewise, by providing very thin sheet metal for the envelope, the introduction of the rasp teeth can be facilitated, and these may be designed with a particular sharp edge and thus produce a good cut. Most preferably, the envelope surrounds the support unit essentially completely, as shown in the figures, with the exception of the back end of the rasp, on which adapter 2 is attached. The envelope is attached in a nonmoving manner to the support unit.

The form of the rasp teeth can be selected extensively in an arbitrary manner. Rasp teeth formed as rectangles, triangles or round may be provided. Further, they may be ovally shaped rasp teeth as well as rasp teeth, which have one or more concavities or convexities along their outer cutting edge.

The dimensioning and the shaping of the support unit can also be freely selected within broad limits, whereby it basically applies that the thinner the material of envelope 4 is selected, the smaller the intrinsic stability will be of the envelope, and thus more support places must be prepared for the envelope to be supported by the support unit.

FIG. 4 shows a cutaway representation through a support unit 3', which is essentially constructed in hemispherical shape. Ribs 15 are also provided, which form the bearing surface for the envelope of metal with rasp teeth, which is adapted to the support unit and also is hemispherical in shape, but is not shown. The ribs are separated from one another by channels 16. In addition to channels 16 running horizontally in FIG. 4, one of which is shown with dashed lines, vertically running channels 17 may also be provided, one channel of which is also illustrated by dashed lines. Support unit 3' also has a connection for adapter 2, not shown, as in the case of support 3. Adapter 2 may be screwed on the inside, e.g., or may be joined with the latter by a plug connection. The adapter is generally not designed as a disposable part and is detached from the rasp after rasp 1 is used.

After the use of the rasp, the latter can be discarded. It is possible to separate the rasp by breaking it up into its basic materials, e.g., plastic and metal or aluminum and steel and to introduce these base materials accordingly, for reutilization or combustion.

We claim:

1. A rasp useful as a one-time use bone rasp, the rasp comprising:
   a support unit having an outer shape essentially determining an outer form shape of the rasp, the support unit having several support elements distributed thereon;
   an envelope of metal material surrounding said inner support unit and applied over the several support elements of the support unit, said envelope having a plurality of rasp teeth disposed thereon.

2. A rasp according to claim 1, wherein said support unit has a longitudinally extended form from a front end to a back end and that widens at its back end.

3. A rasp according to claim 1, wherein said support unit has an essentially hemispherical shape.

4. A rasp according to one of claim 1, wherein said several support elements comprise ribs, to which ribs the envelope is applied to said support unit.

5. A rasp according to claim 4, wherein said support unit has several hollow spaces formed between said ribs, which hollow spaces are joined with openings of said rasp teeth.

6. A rasp according to claim 1, wherein said support unit has a connection for joining said support unit with a treatment machine producing an oscillating or rotating motion.

7. A rasp according to claim 1, wherein said support unit has a connection for joining said support unit with a connection for an adaptor piece for joining with a treatment machine producing an oscillating or rotating action.

8. A rasp according to claim 1, wherein said support unit is formed of aluminum or plastic.

9. A rasp according to claim 1, wherein said envelope is formed of sheet metal with a thickness of 0.2 mm to 4.0 mm.

10. A process for the production of a rasp useful as a one-time use bone rasp, the process comprising:
    (a) providing a support unit having an outer shape essentially determining an outer form shape of the rasp, and with several support elements distributed thereon;
    (b) providing an envelope of metal material having a plurality of rasp teeth disposed thereon, the envelope having an inner form generally conforming to the outer form of the support unit, and
    (c) placing said envelope at least partially over said support unit and attaching the envelope to the several support elements of the support unit.

11. A process according to claim 10 wherein the envelope provide is selected from a one-part and multi-part envelope.

12. A process according to claim 10, wherein said envelope is provided in one part by deep-drawing.

13. A process according to claim 10, wherein said envelope is provided as a multi-art envelope, and that said envelope parts are joined together prior to attaching said envelope to said support unit.

14. A process according to claim 10 wherein said envelope is provided as a multi-part envelope, and that said envelope parts and the support unit are joined to form an essentially closed envelope.

\* \* \* \* \*